United States Patent [19]

Dahlbom et al.

[11] 3,959,311

[45] May 25, 1976

[54] OXOTREMORINE ANTAGONISTS

[75] Inventors: Johan Richard Dahlbom, Sodertalje;
Bo Lennart Karlen, Skarholmen;
Sune Gunnar Lindgren, Vallentuna,
all of Sweden

[73] Assignee: Aktiebolaget Astra, Sodertalje,
Sweden

[22] Filed: May 24, 1974

[21] Appl. No.: 473,190

Related U.S. Application Data

[63] Continuation of Ser. No. 203,828, Dec. 1, 1971, abandoned, which is a continuation-in-part of Ser. No. 774,530, Nov. 8, 1968, abandoned.

[30] Foreign Application Priority Data

Nov. 9, 1967 United Kingdom............... 51146/67

[52] U.S. Cl. ................... 260/326.5 FL; 260/239 B;
260/239 BF; 260/293.71; 260/293.86;
260/293.87; 260/326.43; 260/326.85;
424/267; 424/274
[51] Int. Cl.²............... C07D 295/12; C07D 207/12
[58] Field of Search............. 260/326.5 FL, 293.71,
260/326.25

[56] References Cited
UNITED STATES PATENTS

| | | | |
|---|---|---|---|
| 3,354,178 | 11/1967 | Dickinson | 260/326.3 |
| 3,856,790 | 12/1974 | Freed et al. | 260/326.5 FL |

FOREIGN PATENTS OR APPLICATIONS

| | | | |
|---|---|---|---|
| 1,805,029 | 6/1969 | Germany | 260/293.71 |

OTHER PUBLICATIONS

C. R. Acad. Sc., Paris 264:2250–2253, (1967), Series D, Levy et al.

*Primary Examiner*—Sherman D. Winters
*Attorney, Agent, or Firm*—Brumbaugh, Graves, Donohue & Raymond

[57] ABSTRACT

A new class of amino-imide compounds is disclosed in which a 2-oxo-cycloalkylimide group and an amino group are joined by a chain containing acetylenic unsaturation. The compounds are effective to antagonize the tremorogenic effect of oxotremorine and possess valuable pharmaceutical properties due to a strong central anti-cholinergic effect.

2 Claims, No Drawings

OXOTREMORINE ANTAGONISTS

This is a continuation of application Ser. No. 203,828, filed Dec. 1, 1971, now abandoned, which in turn is a continuation-in-part of application Ser. No. 774,530, filed Nov. 8, 1968, now abandoned.

The present invention relates to new compounds represented by the formula:

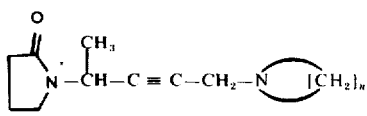

where $n$ ranges between 4 and 6, the therapeutically acceptable salts of these compounds, and pharmaceutical preparations containing these new compounds and their salts.

The above class of compounds is made up of the three following compounds:

N-(1-methyl-4-pyrrolidino-2-butynyl)-pyrrolidin-2-one (when $n = 4$);
N-(1-methyl-4-piperidino-2-butynyl)-pyrrolidin-2-one (when $n = 5$); and
N-1-methyl-4-perhydroazeopin-2-butynyl)-pyrrolidin-2-one (when $n = 6$).

For some years oxotremorine [N-(4-pyrrolidino-2-butynyl)-pyrrolidin-2-one] has been used to induce tremors and spacticity in several species of laboratory animals. It induces violent generalized tremors, spasticity, hypokinesia and parasympathomimetic effects immediately after injection by intravenous routes. The compound thus produces both central and peripheral cholinergic reactions.

A number of drugs are known, such as atropine and caramiphen (1-phenylcyclopentanecarboxylic acid 2-diethylaminoethyl ester) which will antagonize the oxotremorine-induced tremor. They, however, have the side effect of antagonizing the peripheral cholinergic effects of oxotremorine.

The novel compounds of the present invention have unexpectedly been found to exhibit a greater potency than the compounds of the prior art. They have a high specificity as antagonists of the tremoromimetic effects of oxotremorine, i.e., they are characterized by only slight peripheral anti-cholinergic effects.

The compounds of the present invention block the central cholinergic effects caused by oxotremorine, i.e., the motor disturbances, in the same low doses as atropine, while the effect on the peripheral cholinergic symptoms are less pronounced, thus granting the compounds of the invention a high degree of specificity as centrally acting anti-cholinergic agents.

In order to obtain a central anti-cholinergic effect, it is necessary that the compounds of the present invention be capable of penetrating into the brain. Accordingly, when used as oxotremorine antagonists, the compounds should preferably be in the free base form. It will be obvious to those skilled in the art, however, that in the preparation of these compounds it may be convenient to prepare the non-toxic or therapeutically acceptable salts to simplify steps such as fractional crystallization. Accordingly, it will be understood that the typical therapeutically acceptable salts are included within the present invention. Such salts include, but are not limited to, the hyrohalides, especially hydrochloric and hydrobromic acid, and the salts of sulfuric acid, phosphoric acid, acetic acid, tartaric acid, citric acid, and succinic acid. The hydrochloric and hydrobromic acids are preferred because of their ready availability. Manifestly, may other therapeutically acceptable salts will be obvious to those skilled in the art, and all such salts may be employed in the present invention.

As is well known in the art, the tremoromimetic effects of oxotremorine has been proposed as a pharmacological model of Parkinson's disease. The fact that the compounds of the present invention have a high specificity in antagonizing the tremoromimetic effect of oxotremorine suggests, therefore, that they may also be useful in the treatment of Parkinson's disease.

In the Table below, the central and peripheral anti-cholinergic effects in mice of some compounds of the claimed invention are given in comparison with the corresponding effect of atropine and benzhexol, two standard remedies in the treatment of Parkinson's disease. As a standard for the central effect, the dose in mg/kg which inhibits the effect of 150 μg/kg of oxotremorine upon intravenous administration is given. This "tremorolytic" dose is designated as T. As a standard for the peripheral effect the dose of the compound in mg/kg, which doubles the diameter of the pupil, is given. This "mydriatic" dose is designated as M. The ratio between M and T will constitute a standard for specific central effect of the substance. A higher value for M/T corresponds to a higher specificity.

Table

| Compound | Mydriatic Dose (M) | Tremorolytic Dose (T) | M/T |
|---|---|---|---|
| atropine | 0.15 | 0.19 | 0.79 |
| benzhexol | 1.15 | 5.5 | 0.21 |
| N-(1-methyl-4-perhydro-azepino-2-butynyl)-pyrrolidin-2-one | 2.0 | 0.32 | 6.25 |
| N-(1-methyl-4-pyrrolindino-2-butynyl)-pyrrolidin-2-one | 0.62 | 0.19 | 3.26 |

In addition to the above demonstrated specificity of the compounds of the present invention for the central nervous system (CNS), it is also possible to demonstrate their greater CNS specificity by using other test procedures to measure the relative ability of the test compounds to affect the central and peripheral nervous systems, and comparing the corrsponding effects demonstrated by prior art compounds.

The potency of the compounds of the present invention upon the CNS has been found to be greater than that exhibited by a number of homologous compounds. It was tested in the following manner:

Four or more groups, each containing six female mice weighing 22 to 26 grams, were selected. To establish a control, each member of the first group was dosed in sequence with oxotremorine in the absence of any test compound. The tremors in all mice were graded three minutes after administration according to the grading scale set forth in Dahlbom et al. U.S. Pat. No. 3,444,171. The median effective dose of oxotremorine for the control group was determined using the "Up-and-Down Method for Small Samples" described by W. J. Dixon in *Journal of the American Statistical Association*, Volume 60, pages 967–978 (1965).

In the Dixon method the first animal is treated at an arbitrarily selected level and the presence or absence of tremor response is noted. An increased or decreased dosage is then selected according to the schedule specified by the Dixon procedure for the second animal which would tend to produce a change in the tremor response. (For example, if the first dosage produced a tremor, the second animal would be treated at a lower dosage to see if no tremor would result.) The procedure is repeated until all six mice have been tested. If, following the sequence of testing specified by Dixon, all mice of the group showed the same tremor response (all negative or all positive), the group was increased until a change in response was found in two mice.

After the median effective dose for the control group had been established, subsequent groups of animals were treated with the test compound by interperitoneal injection and, ten minutes thereafter, oxotremorine was injected. For each test group, the increased median effective dose of oxotremorine was determined in the same manner.

The following solutions of the compounds of the present invention were used: for N-(1-methyl-4-pyrrolidino-2-butynyl)-pyrrolidin-2-one, 3,55 mg. of the oxalate salt (1 mole of base : 1.5 moles oxalic acid = mol. wt. of 355.5) per 1 ml. of normal saline; for N-(1-methyl-4-piperidino-2-butynyl)-pyrrolidin-2-one, 3.24 mg. of the monooxalate salt (mol. wt. = 324.4) per 1 mg. of normal saline; and for N-(1-methyl-4-perhydroazepino-2-butynyl)-pyrrolidin-2-one, 3.38 mg. of the monooxalate salt (mol. wt. = 338.5) per 1 ml. of normal saline.

For each group of test animals, a series of dosage levels of test compound, and the corresponding median effective doses of oxotremorine required to give the same tremoromimetic response, were measured. The test showed that the median effective dose of oxotremorine was directly proportional to the amount of oxotremorine antagonist administered.

To compare the potency of the test compound the affinity constant was obtained from the data. The affinity constant is that concentration of test compound which when administered blocks the oxotremorine response so that twice the concentration of oxotremorine is necessary to evoke the same response as was produced in the absence of the test compound.

The Table given below summarizes the results obtained when the three compounds disclosed and claimed herein were tested against atropine and Artane (α-cyclohexyl-α-phenyl-1-piperidine-propanol) and compounds Al-301 and Al-302 which have the structures given below:

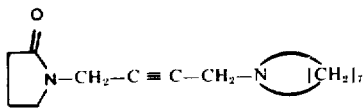

(AL-302)

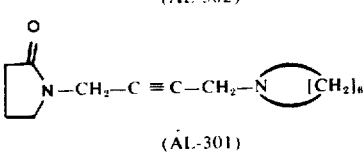

(AL-301)

Both of these compounds differ from the compounds claimed herein by lacking a methyl branching on the butynyl chain, and, in the case of Al-302, the presence of one extra methylene group in the heterocyclic amino group.

Table

| Compound | Affinity Constant Dose (moles per kilogram) | Ratio |
|---|---|---|
| N-(1-methyl-4-pyrrolidino-2-butynyl)-pyrrolidin-2-one | $4.4 \times 10^{-7}$ | 17.0 |
| N-(1-methyl-4-piperidino-2-butynyl)-pyrrolidin-2-one | $8.7 \times 10^{-7}$ | 8.5 |
| N-(1-methyl-4-perhydroazepino-2-butynyl)-pyrrolidin-2-one | $8.2 \times 10^{-7}$ | 9.0 |
| Prior Art Compounds | | |
| AL-301 | $7.4 \times 10^{-6}$ | 1.0 |
| atropine | $2.8 \times 10^{-6}$ | 2.6 |
| Artane | $4.7 \times 10^{-6}$ | 1.8 |

The above data show that the compounds claimed herein have a lower affinity constant dosage than the prior art, thereby showing a higher potency. They are therefor more potent antagonists for the tremoromimetic effects of oxotremorine.

A ratio of the affinity constant dosages with AL-301 being set equal to 1.0 shows that the potencies of Artane and atropine are 1.8 and 2.6, respectively. In contrast, the compounds of the prior art exhibit a much higher potency. For example, when $n$ is equal to 4 in the structural formula of the claimed compounds given in the beginning of this specification, the ratio is 17. When $n$ is equal to 5 and 6, the ratios are 8.5 and 9.0, respectively. The claimed compounds are therefore all at least 8.5 times more potent than the most similar prior art compound. The structurally dissimilar Artane and atropine, which are the drugs of choice for antagonizing the tremorlytic effects of oxotremorine, have potencies which are about 2 or 3 times less than the compounds claimed herein.

The compounds of the present invention may be prepared by the reaction between an acetylenic lactam, formaldehyde and an amine:

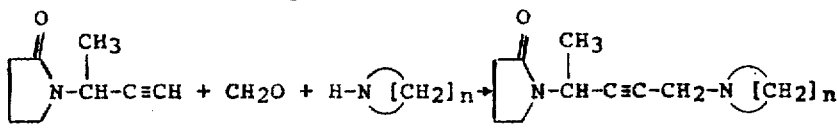

where *n* is defined as above.

According to an alternative method an acetylenic diamine is treated with a halogenoacyl halogenide and the resulting product is ring-closed to the desired product:

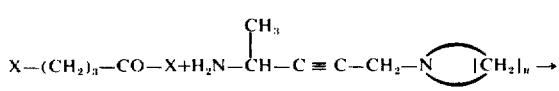

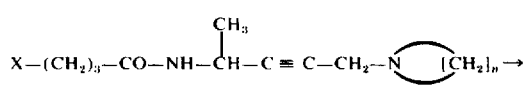

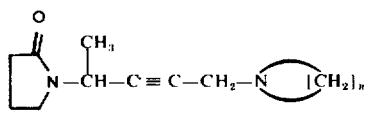

where *n* is defined as above and X is a halogen.

The following are particularly preferred procedures for preparing the compounds of the claimed invention:

EXAMPLE 1 (n = 4)

Preparation of
N-(1-methyl-4-pyrrolidino-2-butynyl)-pyrrolidin-2-one sesquioxalate The compound 3-amino-1-butyne was treated with γ-chlorobutyryl chloride giving 3-(γ-chlorobutyramido)-1-butyne, m.p. 50°–51°C., which was ring-closed to N-(1-methylpropargyl)-pyrrolidin-2-one with the boiling point 71°C. at 0.8 mm Hg. Treatment of this product with formaldehyde and pyrrolidine yielded a reaction product which was isolated and purified as the sesquioxalate. It melted at 117°–119°C. after recrystallization from ethanol-ether.

EXAMPLE 2 (n = 5)

Preparation of
N-(1-methyl-4-piperidino-2-butynyl)-pyrrolidin-2-one

The compound N-(1-methylpropargyl)-pyrrolidin-2-one was treated with formaldehyde and piperidine (pentamethylenimine) to yield N-(1-methyl-4-piperidino-2-butynyl)-pyrrolidin-2-one which boiled at 130°C. at 0.3 mm Hg.

EXAMPLE 3 (n = 6)

Preparation of
N-(1-methyl-4-perhydroazepino-2-butynyl)-pyrrolidin-2-one oxalate Treatment of N-(1-methylpropargyl)-pyrrolidin-2-one with formaldehyde and perphydroazepine(hexamethylenimine) as described in the foregoing Examples yielded a reaction product which was isolated and purified as the oxalate. It had a melting point of 116°–117°C.

It will be appreciated that the foregoing is intended to be illustrative and that modifications of the claimed invention will be apparent upon reading the foregoing. The claims define the invention.

We claim:

1. A compound having the formula

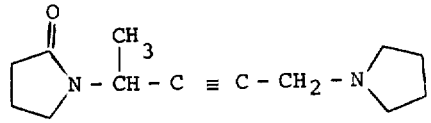

or a therapeutically acceptable salt thereof.

2. A compound having the formula

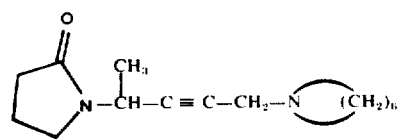

or a therapeutically acceptable salt thereof.

* * * * *